United States Patent [19]

Pantini et al.

[11] Patent Number: 5,354,552
[45] Date of Patent: Oct. 11, 1994

[54] PROCESS FOR PREPARING CLEANSING EMULSIONS FOR BEAUTY TREATMENT AND COSMETIC PRODUCTS THEREOF

[75] Inventors: Giovanni Pantini, Milan; Mario Visca, Alessandria, both of Italy

[73] Assignee: Ausimont S.r.L., Milan, Italy

[21] Appl. No.: 13,478

[22] Filed: Jan. 29, 1993

Related U.S. Application Data

[60] Continuation of Ser. No. 727,699, Jul. 10, 1991, abandoned, which is a division of Ser. No. 411,312, Sep. 22, 1989, Pat. No. 5,093,023.

[30] Foreign Application Priority Data

Sep. 23, 1988 [IT] Italy .................. 22053 A/88

[51] Int. Cl.⁵ .................. A61K 7/50
[52] U.S. Cl. .................. 424/401; 424/78.03; 424/70; 514/937; 514/969; 252/DIG. 2; 252/DIG. 14
[58] Field of Search .................. 424/401, 78.03, 70; 514/937, 969; 252/DIG. 2, DIG. 14

[56] References Cited

U.S. PATENT DOCUMENTS

| | | | |
|---|---|---|---|
| 3,665,041 | 5/1972 | Sianesi et al. | 252/67 |
| 3,669,891 | 6/1972 | Greenwood et al. | 252/90 |
| 3,713,404 | 1/1973 | Lavo et al. | 252/DIG. 1 |
| 3,715,378 | 2/1973 | Sianesi et al. | 252/78.1 |
| 3,763,053 | 10/1973 | Bills | 252/357 |
| 3,763,631 | 10/1973 | Horn et al. | 55/96 |
| 3,959,462 | 5/1976 | Parks et al. | 252/171.23 |
| 3,972,998 | 8/1976 | Keiner | 252/554 |
| 4,066,746 | 1/1978 | Callingham et al. | 8/405 |
| 4,523,039 | 6/1985 | Lagow et al. | 568/615 |
| 4,803,067 | 2/1989 | Brunetta et al. | 424/63 |

OTHER PUBLICATIONS

Grant & Hackh's Chemical Dictionary, Fifth Edition, McGraw-Hill, Inc.
"Perfluoropolyethers for Cosmetics", Drug & Cosmetic Industry, Sep. 1988, by Pantini, et al.

Primary Examiner—Paul R. Michl
Assistant Examiner—Raj Bawa
Attorney, Agent, or Firm—Morgan & Finnegan

[57] ABSTRACT

A process and composition for treating skin and hair that reduces the redistribution of sebum on the skin and hair of normal and seborrheic subjects and normalizes the redistribution of sebum on the skin and hair of asteatosic persons. The composition includes a polyfluoroether with perfluoroalkyl end groups in combination with at least one surfactant having an interface tension less than or equal to 15 dynes/cm with the polyfluoroether, at least one thickening agent, water and optionally a polyalcohol, foam booster, softener, dye, preservative, opacifier, or sequestering agent.

3 Claims, 2 Drawing Sheets

PROCESS FOR PREPARING CLEANSING EMULSIONS FOR BEAUTY TREATMENT AND COSMETIC PRODUCTS THEREOF

This is an continuation application of prior application Ser. No. 07/727,699, filed Jul. 10, 1991, now abandoned, which in turn is a divisional of application Ser. No. 07/411,312, filed Sep. 22, 1989, now U.S. Pat. No. 5,093,023.

FIELD OF THE INVENTION

The present invention relates to a process for preparing cleansing emulsions for beauty treatment. It relates also to novel cosmetic products.

BACKGROUND OF THE INVENTION

An important problem in skin and hair cleansing is the effect of re-distribution of sebum (the so-called "rebound" effect).

Several additives were proposed in the past to reduce the sebum rebound effect. In particular, in U.S. Pat. Nos. 3,972,998 and 3,959,462, hereby incorporated by reference, the use of film-forming fluorinated resins is disclosed. Unfortunately, the use of film-forming resins has drawbacks. They are difficult to eliminate, can lead to accumulation phenomena, and can cause toxicity problems.

Applicants have surprisingly found now that the effect of re-distribution of sebum on skin and hair may be reduced without running into the above mentioned drawbacks, if cleansing compositions are used, which contain perfluoropolyethers having perfluoroalkyl end groups.

Also, the present Applicants have surprisingly found that the use of the same compositions normalizes the redistribution of sebum on the skin of asteatosic subjects.

DETAILED DESCRIPTION OF THE INVENTION

Figure 1:
FIG. 1 is a photograph of observations made at 2,100× magnification using a scanning electron microscope.

It is known that the perfluoropolyethers containing perfluoroalkyl end groups are insoluble in nearly all of the solvents and are water-repellant and oil-repellant. Their introduction, in a stable condition, in cleansing compositions for beauty treatment is a very difficult problem to be solved. The present Applicants have surprisingly found now that a stable emulsion of perfluoropolyethers containing perfluoroalkyl end groups in cleansing compositions for beauty treatment can be achieved using a particular preparation process. It is disclosed below.

An object of the present invention is therefore of supplying a process for preparing cleansing emulsions for beauty treatment.

This object is achieved using a process for preparing cleansing emulsions for beauty treatment according to the present invention. This process comprises:

1. Using a perfluoropolyether containing perfluoroalkyl end groups, and one or more substance(s) selected from the group consisting of surfactants, oils, fats, and polyalcohols having a low interface tension with the perfluoropolyether, with at least one of these substances being a surfactant;
2. Mixing the substances selected from the surfactants, oils, fats, and polyalcohols with water, heating to a temperature that a homogeneous mixture or emulsion is obtained and deaerating mixture or emulusion;
3. Melting thickening substances and any foam-supporting substances and diluting with water until a medium-viscosity solution is obtained;
4. Adding the perfluoropolyether with strong stirring to the mixture (2) above, or to the mixture (3) above;
5. Mixing the mixtures (2) and (3) together and deaerating the obtained mixture;
6. Any possible preservatives, dyes, perfumes, softeners, opacifiers and sequestering agents are added to the mixture (2), or to the mixture (3), or to the mixture (5); and
7. Cooling the whole mixture with stirring.

The perfluoropolyethers having perfluoroalkyl end groups, i.e., without functional groups, are well-known products. They are generally obtained as mixtures of compounds having a molecular weight comprised within a certain range.

These perfluoropolyethers are disclosed, together with the route for preparing them, in a plurality of documents, among which U.K. patent No. 1,104,482; U.S. Pat. Nos. 3,242,218; 3,665,041; 3,715,378; and 4,523,039 and European patent application Nos. 148,482 U.S. Pat. No. 4,848,648 and 191,490 abandoned, all hereby incorporated by reference.

Among the suitable perfluoropolyethers, are those characterized by the presence of one or more of the following repeating perfluoro-oxyalkylene units:

$(CF_2-CF_2O)$;     (a)
$(CF_2O)$;          b)

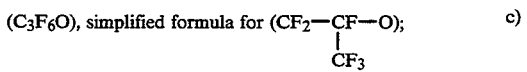

$(C_3F_6O)$, simplified formula for $(CF_2-CF-O)$;     c)
$\phantom{(C_3F_6O), simplified formula for (CF_2-}CF_3$

$(CF_2O-CF_2-CF_2O)$;    d)
$(CF_2-CF_2-CF_2O)$;     e)

$(CFO)$;    f)
$|$
$CF_3$

$$\begin{array}{ccc} CF_3 & R_fIII & R_fIII \\ | & | & | \\ (C-O-C-\!\!\!-\!\!\!-C-O) \\ | & | & | \\ CF_3 & R_fIII & R_fIII \end{array} \quad \text{g)}$$

wherein the $R_fIII$ groups, which may be equal to, or different from, one another, are a fluorine atom, or a perfluoroalkyl group.

According to a preferred embodiment, the perfluoropolyethers suitable for the present invention contain the following individual perfluoro-oxy-alkylene units, or combinations of perfluoro-oxy-alkylene units:

(I) $(CF_2\text{-}CF_2O)$ and $(CF_2O)$, with such units being randomly distributed along the perfluoropolyether chain; or

$(CF_2-CFO)$ and $(CFXO)$,     (II)
$\phantom{(CF_2-}|$
$\phantom{(CF_2-}CF_3$

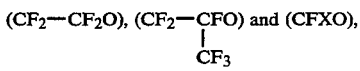 (III)

wherein X is either F or CF$_3$, with such units being randomly distributed along the perfluoropolyether chain; or

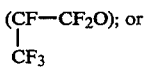 (IV)

(CF$_2$—CF$_2$—CF$_2$O); or (V)
(CF$_2$—CF$_2$O); or (VI)

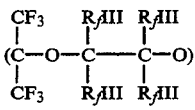 (VII)

wherein the R$_f$III groups, which may be either equal to, or different from, one another, are a fluorine atom, or a perfluoroalkyl group; or
(CF$_2$O-CF$_2$-CF$_2$O).

Also the perfluoropolyethers are suitable, which contain perfluorooxetanic rings

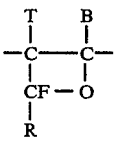

or

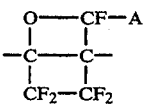

wherein, T, B and R, which may be either equal to, or different from, one another, are perfluoro-oxyalkyl radicals, perfluoro-polyoxyalkyl radicals or perfluoroalkyl radicals, and A is a perfluoro-oxyalkyl radical, or perfluoropolyoxyalkyl, or a perfluoroalkyl radical.

Examples of suitable perfluoropolyethers containing repeating perfluoro-oxyalkylene units are those belonging to the following classes:

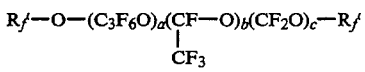 (a)

wherein:

R$_f$ and R$_f$', which may either be equal to, or different from, each other, are selected from the group consisting of CF$_3$, C$_2$F$_5$ and C$_3$F$_7$;
the C$_3$F$_6$O (oxy-trifluoromethyl-trifluoroethylene),

and (CF$_2$O) units are randomly distributed along the polymer chain;
a is an integer;
b and c are either integers or zero; when the total of (b+c) is different from zero, the ratio of a/(b+c) is comprised within the range of from 5 to 40.

(b) 

wherein:
the C$_2$F$_4$O and CF$_2$O units are randomly distributed along the chain;
d and e are integers;
the ratio of d/e is comprised within the range of from 0.3 to 5.

(c) CF$_3$O-(C$_3$F$_6$O)$_f$(C$_2$F$_4$O)$_g$(CFXO)$_h$-CF$_3$
wherein:
the C$_3$F$_6$O, C$_2$F$_4$O and CFXO units are randomly distributed along the chain;
X is either F or CF$_3$;
f, g and h are integers;
the ratio of f/(g+h) is comprised within the range of from 1 to 50; and
the ratio of g/h is comprised within the range of from 1 to 10;

(d) 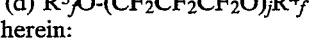
wherein:
R$^3_f$ and R$^4_f$, which may be either equal to, or different from each other, are either -CF$_3$ or -C$_2$F$_5$ and j is an integer.

The average molecular weight of perfluoropolyethers suitable for use in the instant invention is generally comprised within the range of from 500 to 20,000. Their average molecular weight is preferably comprised within the range of from 1,500 to 10,000.

The contents of perfluoropolyether in the cleansing emulsions is generally comprised within the range of from 0.01 up to 20% by weight, and is preferably comprised within the range of from 0.05 up to 5%.

The interface tension with the perfluoropolyether of the surfactants, oils, fats and polyalcohols suitable for use in the process according to the present invention is generally lower than, or equal to 15 dyne.cm$^{-1}$, and is preferably lower than, or equal to, 12 dyne.cm$^{-1}$.

Suitable surfactants are, for exemplifying purposes: coco-amphoglycinate, coco-amido-betaine, lauroyl sarcosinate, DEA oleylamide (a mixture of diethanolamides and oleic acid), DEA coco-amide (a mixture of diethanolamides and coconut fatty acids), polyethyleneglycol-6-caprylic-capric triglycerides, dodecylamine oxide, polyethyleneglycol-7 coco acid monoglycerides and diglycerides, polyethyleneglycol-78 coco mono- and di-glycerides, sodium laurylether sulfate, 2.5 ethylene oxide and stearyl-dimethyl-benzyl-ammonium chloride.

Suitable oils and fats are, e.g., squalane, staeric acid and avocado pear oil.

A suitable polyalcohol is, e.g., glycerol.

The mixture of substances selected from among the group consisting of surfactants, oils, fats, and polyalcohols with water is heated up to a selected temperature comprised within the range of those temperatures which are commonly used in the preparation of cleansing emulsions, i.e., of from 25° C. up to 75° C., and preferably comprised within the range of from 40° C. up to 75° C.

The mixture of thickeners for viscosity purposes and of possible foam supporting substance with water is also heated up to a temperature selected within the range of temperatures commonly used in the preparation of cleansing emulsions, i.e., at a temperature comprised within the range of from 25° C. up to 75° C., and preferably of from 40° C. up to 75° C. The viscosity of the mixture is adjusted by means of the addition of water, until a medium-viscosity solution, is obtained. For that purpose, a viscosity usually comprised within the range of from 500 up to 5,000 centipoises (as measured at 25° C.), and preferably of from 1,000 to 2,000 centipoises, is suitable.

The addition of the perfluoropolyether to either of the above mixtures is carried out with strong stirring. For that purpose, an apparatus is used, such as, e.g., a turbine stirrer, which runs at a revolution speed of at least 3,000 rpm, and preferably of at least 5,000 rpm.

The perfluoropolyether is preferably added to the mixture of thickening agents and possible foam supporting agents with water.

Any possible preservatives, dyes, perfumes, softeners, opacifiers, and sequestering agents are preferably the last to be added, i.e., they are added to the mixture of substances selected from among the surfactants, oils, fats, and polyalcohols with the thickeners, the possible foam supporting agents, the perfluoropolyether and water, before the emulsion is cooled.

The so-obtained cleansing emulsions comprise the shampoos, the foam baths, the cleansing milks, the cleansing creams, the bath oils, the liquid soaps and similar compositions for skin and hair cleansing.

The surfactants, the oils, the fats, and the polyalcohols are commonly selected from among those which are customarily used in the preparation of cleansing emulsions for beauty treatment, which simultaneously show a low interface tension with the perfluoropolyether.

The thickeners, and all of the other components are commonly selected from among those which are customarily used in the preparation of cleansing emulsions for beauty treatment.

Suitable thickeners are, e.g., xanthan gum, guar gum and PEG 6000 (polyethylene glycol) distearate.

Another object of the present invention are the cleansing emulsion comprising:
(1) a perfluoropolyether with perfluoroalkyl end groups in an amount comprised within the range of from 0.01 up to 20% by weight;
(2) one or more substance(s) selected from among surfactants, oils, fats, and polyalcohols having a low interface tension with the perfluoropolyether, with at least one of these substances being a surfactant;
(3) one or more thickening agents;
(5) possibly, one or more foam supporting substance(s);
(6) possibly, one or more softeners and/or perfumes and/or dyes and/or preservatives and/or opacifiers and/or sequestering agents.

A further object of the present invention are foam baths, cleansing milks, bath oils and liquid soaps characterized in that they contain, besides their usual components from 0 01% up to 20% by weight of perfluoropolyethers with perfluoroalkyl end groups.

The main advantages of the present invention can be summarized as follows:
  stable emulsions of the perfluoropolyether in the cleansing compositions for skin and hair are obtained;
  after washing, a reduction is obtained in the rebound effect on hair and on seborrheic skin;
  a normalization of the redistribution of sebum on skin of asteatosic subjects is obtained after washing.

EXAMPLES

The following examples are merely illustrative, and should not be considered to limit the present invention.

Example 1

For comparative purposes a shampoo not containing a perfluoropolyether was prepared. The shampoo had the following composition, by weight:

| | |
|---|---|
| A) alkylamidobetaine | 5.0% |
| B) alkylamidoamine N-oxide | 4.0% |
| C) coco-ampho-glycinate | 5.0% |
| D) sodium laurylether sulfate | 5.0% |
| E) ethoxylated coco glycerides | 4.0% |
| F) sodium chloride | 1.0% |
| G) polyethyleneglycol 6000 distearate | 3.0% |
| H) deionized water | q.s. up to 100% |
| I) preservatives, dyes, perfumes | q.s. |

The shampoo was prepared as follows:
(1) (A), (C) and (D) were mixed with each other, together with a portion of (H); then (F) was added and the whole mixture carefully deaerated;
(2) (B) and (E) were melted together with (G) and water at 75° C. was added, until a pourable solution is obtained;
(3) (2) was slowly added to (1), and the so-obtained mixture was deaerated;
(4) (I) was added;
(5) the obtained mass was cooled with simultaneous stirring.

Example 2

A shampoo was prepared which was identical to the shampoo of Example 1, but which additionally contained 1% of a perfluoropolyether with perfluoroalkyl end groups. The perfluoropolyether was Fomblin HC/04 by Montefluos S.p.A. having the formula:

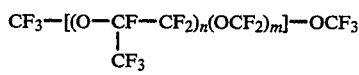

wherein n/m is comprised within the range of from 20 to 40.

This perfluoropolyether has an average molecular weight of 1,500 and a viscosity of 35 cSt at 20° C.

The shampoo had the following composition, by weight:

| | |
|---|---|
| A) alkylamidobetaine | 5.0% |
| B) alkylamidoamine N-oxide | 4.0% |
| C) coco-ampho-glycinate | 5.0% |
| D) sodium laurylether sulfate | 5.0% |
| E) ethoxylated coco glycerides | 4.0% |
| F) sodium chloride | 1.0% |
| G) polyethyleneglycol 6000 distearate | 3.0% |
| H) perfluoropolyether Fomblin HC/04 | 1.0% |
| I) deionized water | q.s. up to 100% |
| J) preservatives, dyes, perfumes | q.s. |

The shampoo was prepared as follows:
(1) (A), (C) and (D) were mixed with each other, together with a portion of (I); then (F) was added and the whole mixture carefully deaerated;
(2) (B) and (E) were melted together with (G) and water at 75° C. was added, until a pourable solution is obtained;

(3) (H) was dispersed throughout the mixture (2) using a turbine mixer;
(4) (3) was slowly added to (1), and the whole mixture deaerated;
(5) (J) was added;
(6) the obtained mass was cooled with simultaneous stirring.

The shampoo according to the present invention, and the comparative shampoo, not containing perfluoropolyether, Were evaluated as follows.

A preliminary study under the scanning electron microscope was carried out on seborrheic hair before and after the application of the shampoo which contained perfluoropolyether. Hair samples supplied by six seborrheic patients were studied. The hair samples were drawn from the same scalp region of all the patients two days after the cleansing with the placebo shampoo, not containing perfluoropolyether in its formulation (Example 1).

A second taking was carried out after one month of twice-weekly washings with the same shampoo containing 1% of perfluoropolyether (Example 2).

Each hair was drawn by means of suitable tweezers, and, without any preliminary treatments, were placed on a support, on which they were fastened using a bis-adhesive tape. They were then metallized with 200 Å of gold-platinum on a Balzers MED 010 metallizer, and were observed by means of the Philips 505 scanning electron microscope.

The individual hairs were observed at their suprabulbar region.

The observation was carried out at magnifications comprised within the range of from 1,100 up to 8,800. Under basal reference condition (see FIG. 1, at 2,100× magnifications), the presence is observed on hair surface of an "induitus" characterized by structure-lacking polycyclic and semispherical masses or protrusions, which hindered, at least partially, the normal morphology of cuticular geometry.

These finds were identical in all of the analyzed samples.

Figure 2:
FIG. 2 is a photograph of observations made at 2,000× magnification using a scanning electron microscope.

The observation of hair after the treatment with the shampoo which contained perfluoropolyether (see FIG. 2, at 2,000× magnifications) made possible a meaningful decrease to be evidenced in the presence of this induitus, which is normally to be ascribed to the presence of sebum.

Example 3

A foam bath not containing perfluoropolyether was prepared for comparative purposes. The foam bath had the following composition by weight:

| | |
|---|---|
| A) sodium laurylether sulfate | 15% |
| B) coco-ampho-glycinate | 4.0% |
| C) alkylamidobetaine | 10.0% |
| D) ethoxylated coco glycerides | 6.0% |
| E) alkylamidoamine N-oxide | 5.0% |
| F) polyethyleneglycol 6000 distearate | 2.0% |
| G) xanthan gum | 2.0% |
| H) sodium chloride | 1.0% |
| I) deionized water | q.s. up to 100% |
| j) preservatives, dyes, perfume | q.s. |

The foam bath was prepared as follows:
(1) (G) was dispersed in a portion of (I) and in (H), until a homogeneous gel was obtained; this latter was then deaerated, and (A), (B) and (C) added under vacuum;
(2) (D), (E) and (F) were melted at 75° C., and water at 75° C. was added, until a pourable solution was obtained;
(3) (2) is slowly added to (1), and the whole mixture was deaerated;
(4) (J) was added;
(5) the obtained mass was cooled with simultaneous stirring.

Example 4

A foam bath was prepared which was identical to the foam bath of Example 3, but additionally containing 1% of a perfluoropolyether with perfluoroalkyl end groups. The perfluoropolyether was Fomblin HC/R by Montefluos S.p.A., having the same formula as specified in Example 2.

This perfluoropolyether had an average molecular weight of 6,600 and a viscosity of 1,500 cSt at 20° C.

The foam bath had the following composition, by weight:

| | |
|---|---|
| A) sodium laurylether sulfate | 15% |
| B) coco-ampho-glcyinate | 8.0% |
| C) alkylamidobetaine | 10.0% |
| D) ethoxylated coco glycerides | 6.0% |
| E) alkylamidoamine N-oxide | 5.0% |
| F) polyethyleneglycol 6000 ditearate | 2.0% |
| G) xanthan gum | 2.0% |
| H) sodium chloride | 1.0% |
| I) deionized water | q.s. up to 100% |
| J) perfluoropolyether Fomblin HC/R | 1.0% |
| J') preservatives, dyes, sequestering agents, perfume | q.s. |

The foam bath was prepared as follows:
(1) (G) was dispersed in a portion of (I) and in (H), until a homogeneous gel was obtained; this latter is then deaerated, and (A), (B) and (C) were added under vacuum;
(2) (D), (E) and (F) were melted at 75° C., and water at 75° C. was added, until a pourable solution was obtained;
(3) (J) was dispersed throughout (2) by means of a turbine stirrer;
(4) (3) was slowly added to (1), and the whole mixture deaerated;
(5) the obtained mass was cooled with simultaneous stirring.

The foam bath according to the present invention (Example 4) and the foam bath not containing perfluoropolyether (Example 3) were evaluated as follows.

The sebacic response of skin to cleansing was determined in vivo. Thirty healthy volunteers from 13 to 81 years old were selected At the objective examination, volunteers' skin appeared to be normal or mixed in 39.6% of cases, seborrheic in 11.4% of cases, asteatosic in 49% of cases. The skin regions submitted to evaluation were: the forehead (at glabella level) and the presternal region (immediately above the sternal angle).

On each subject, in both of these regions two cleansing agents were used, which correspond to the preparations disclosed in Examples 3 and 4. The subjects with normal, mixed or seborrheic skin were taught to use, always at the same time in the morning, for ten consecutive days, the perfluoropolyether-containing cleansing preparate on forehead, and the placebo on the presternal region. The subjects with asteatosic skin were taught to do the contrary.

The determinations of the sebacic response after cleansing were carried out according to two different routes: with the Schwarzhaupt's SM 410 sebometer, and with SEBUMTAPE® adhesive tapes (Cuderm Co., Dallas, U.S.A.; Hermal Pharm. Lab., Oak Hill, U.S.A.).

Such determinations were carried out between 9:00 a.m. and 11:00 a.m., under constant conditions of room temperature and humidity (50%±2% of humidity, 22° C.±1° C.).

The sebometric measurements were carried out:
(1) under basal conditions ("lipid casual level");
(2) soon after a strong washing with 30% isopropanol (with sebometric index being practically zero);
(3) one hour after the cleansing according to (2);
(4) after 24 hours, with the cleansing emulsion being used 1 hour in advance;
(5) after 10 days of daily use, in the morning, of the cleansing emulsion, 1 hour after the last wash.

The Sebumtape strip was simultaneously applied on a skin region immediately adjacent to the region on which the sebometric measurement was carried out, was left on that region for 1 hour, and was then removed, applied onto a piece of thin card of black color, and was finally photographed with a constant magnification.

The measurements carried out under basal conditions confirmed the distribution of the sebometric values by sex, age, and body region.

The sebometric determinations carried out to quantify the response to the cleansing treatment made possible the following results:

In the subjects with normal, mixed, or seborrheic skin, washing with isopropanol leads to considerable increase in seborrheic value already after 1 hour.

After 24 hours (1 hour after the use of the cleansing emulsion), the sebometric values had further increased.

After 10 days of constant use of the cleansing emulsion containing the perfluoropolyether, the treated regions showed a lower average sebometric value than the preceding measurement (i.e., the measurement carried out after 24 hours).

The skin regions treated in the same way with the cleansing system not containing perfluoropolyether had undergone an increase in sebum (rebound effect).

In the subjects with asteatosic skin, the average sebometric increase occurred more slowly, and was a maximum after 10 days of use of the cleansing agent with the perfluoropolyether. On the contrary, in skin regions treated with the placebo, the value remained constantly low.

Such results were confirmed as well by the observation of the photographs of Sebumtapes, in which a decrease was observed in number and in size of black spots (decrease in seborrhea) for subjects with normal, mixed or seborrheic skin treated with perfluoropolyether-containing cleanser. This was contrary to what was observed on subjects with asteatosic skin.

Although the invention has been described in conjunction with specific embodiments, it is evident that many alternative and variations will be apparent to those skilled in the art in light of the foregoing description. Accordingly, the invention is intended to embrace all of the alternatives and variations that fall within the spirit and scope of the appended claims.

What is claimed is:

1. Cleansing emulsions for skin and hair to reduce the redistribution of sebum on skin and hair of normal and seborrheic subjects and to normalize the redistribution of sebum on skin and hair of asteatosic persons, consisting of:
   (1) a perfluoropolyether with perfluoroalkyl end groups having a molecular weight of about 500 to 20,000, in an amount from about 0.01 up to about 20% by weight;
   (2) at least one surfactant having an interface tension less than or equal to 15 dynes/cm with the perfluoropolyether;
   (3) at least one thickening agent;
   (4) water;
   (5) optionally, at least one polyalcohol having an interface tension less than or equal to 15 dynes/cm with the perfluoropolyether;
   (6) optionally, at least one foam booster; and
   (7) optionally, at least one softener, dye, preservative, opacifier, or metal sequestering agent.

2. A method for cleansing skin and hair to reduce the redistribution of sebum on skin and hair of normal and seborrheic subjects and to normalize the redistribution of sebum on skin and hair of asteatosic persons comprising:
   washing with cleansing emulsions consisting of,
   (1) a perfluoropolyether with perfluoroalkyl end groups having a molecular weight of about 500 to 20,000, in an amount from about 0.01 up to about 20% by weight;
   (2) at least one surfactant having an interface tension less than or equal to 15 dynes/cm with the perfluoropolyether;
   (3) at least one thickening agent;
   (4) water;
   (5) optionally, at least one polyalcohol having an interface tension less than or equal to 15 dynes/cm with the perfluoropolyether;
   (6) optionally, at least one foam booster; and
   (7) optionally, at least one softener, perfume, dye, preservative, opacifier, or metal sequestering agent.

3. A method according to claim 2, wherein the polyalcohol is glycerol.

* * * * *